United States Patent [19]

Gruber

[11] Patent Number: 4,849,536

[45] Date of Patent: Jul. 18, 1989

[54] PREPARATION OF ALPHA-CYANOBENZYL ESTERS

[75] Inventor: John M. Gruber, Mountain View, Calif.

[73] Assignee: Sandoz Ltd., Basel, Switzerland

[21] Appl. No.: 150,953

[22] Filed: Feb. 1, 1988

Related U.S. Application Data

[63] Continuation of Ser. No. 18,305, Feb. 24, 1987, abandoned.

[51] Int. Cl.$^4$ ............................................ C07C 121/66
[52] U.S. Cl. ..................................... 558/351; 558/407
[58] Field of Search ................................ 558/351, 407

[56] References Cited

U.S. PATENT DOCUMENTS

| | | | |
|---|---|---|---|
| 3,835,176 | 9/1974 | Matsuo et al. | 558/410 |
| 3,973,035 | 8/1976 | Searle et al. | 514/521 |
| 3,973,036 | 8/1976 | Hirano et al. | 514/531 |
| 3,987,193 | 10/1976 | Davis et al. | 514/531 |
| 4,100,298 | 7/1978 | Davis et al. | 514/510 |
| 4,175,134 | 11/1979 | Davis et al. | 558/407 |
| 4,260,633 | 4/1981 | Anderson et al. | 514/521 |
| 4,411,912 | 10/1983 | Henrick et al. | 514/521 |
| 4,594,198 | 6/1986 | Dong et al. | 558/551 |
| 4,723,027 | 2/1988 | Stoutamire et al. | 558/407 |

OTHER PUBLICATIONS

Weygand et al., *Preparative Organic Chemistry*, p. 372, 1972.

Primary Examiner—Mary C. Lee
Assistant Examiner—Zinna Northington
Attorney, Agent, or Firm—Jacqueline S. Larson

[57] ABSTRACT

A process for the preparation of α-cyanobenzyl esters of cyclopropane carboxylic acids and substituted alkanoic acids by treating a carboxylic acid and a benzaldehyde with a metal cyanide, followed by treatment with a sulfonyl halide.

8 Claims, No Drawings

PREPARATION OF ALPHA-CYANOBENZYL ESTERS

This is a continuation-in-part of Ser. No. 018,305, filed on Feb. 24, 1987, now abandoned.

This invention relates to an improved process for the preparation of α-cyanobenzyl esters of cyclopropane carboxylic acids and substituted alkanoic acids, which esters are active pesticides and form part of the class of compounds known as synthetic pyrethroids.

More particularly, the present invention provides a one-pot, two-reaction process for the preparation of an α-cyano ester of formula (I):

$$W-\overset{O}{\underset{\|}{C}}-O-\overset{CN}{\underset{|}{CH}}-Ar \quad (I)$$

wherein W is an optionally substituted cycloalkyl or substituted alkyl group containing up to 24 carbon atoms, and Ar is a substituted aromatic or heteroaromatic group, which process comprises (a) treating a carboxylic acid of formula W—COOH and an aldehyde of formula (II)

$$\overset{O}{\underset{\|}{HC}}-Ar \quad (II)$$

with an alkali or alkaline earth metal cyanide in an acid acceptor solvent and, optionally, an aprotic solvent, and (b) treating the resulting mixture with a sulfonyl halide.

When W represents an optionally-substituted cycloalkyl group in formula (I), the preferred compounds are those containing a cyclopropyl group of formula (III)

(III)

wherein, each of $R^2$ and $R^3$ is independently $C_{1-6}$alkyl or halogen; or $R^2$ represents hydrogen, and $R^3$ represents $C_{1-6}$alkyl, $C_{1-6}$haloalkyl, $C_{2-6}$alkenyl or $C_{2-6}$haloalkenyl; and each of $R^4$ and $R^5$ is independently $C_{1-6}$alkyl or $R^4$ is hydrogen and $R^5$ is $C_{1-6}$alkyl, $C_{1-6}$haloalkyl, $C_{2-6}$alkenyl or $C_{2-6}$haloalkenyl.

When W represents an optionally substituted benzyl group in formula (I), preferred compounds are those containing a substituted benzyl group of formula (IV)

(IV)

wherein, $R^6$ is $C_{1-6}$alkyl or cyclopropyl;

t is zero, one or two; and each of Y and Z is independently hydrogen, $C_{1-6}$alkyl, $C_{1-6}$haloalkyl, $C_{1-6}$alkoxy, $C_{1-6}$haloalkoxy, halogen or nitro.

When W represents an optionally substituted anilinoalkyl group in formula (I), preferred compounds are those of formula (V)

(V)

wherein, the values of $R^6$, t, Y and Z are as defined hereinabove.

In the practice of the present invention, $R^2$ is preferably methyl or chloro.

$R^3$ is preferably methyl, chloro, isobutenyl, mono- or dichlorovinyl, dibromovinyl, 1,2,2,2-tetrabromethyl, or 1-(2-chloro-3,3,3-trifluoro-1-propenyl).

$R^4$ is preferably methyl.

$R^5$ is preferably methyl, isobutenyl or mono- or dichlorovinyl.

$R^6$ is preferably a branched chain alkyl such as isopropyl.

t is preferably zero or one.

Y is preferably $CF_3$.

Z is preferably methyl, methoxy or chloro.

Ar is preferably a substituted phenyl group and more preferably a group of formula (VI)

(VI)

wherein $R^1$ is hydrogen or fluoro.

Synthetic pyrethroid compounds of formula (I) are known in the art and are disclosed in, for example, U.S. Pat. Nos. 3,835,176; 3,973,035; 3,973,036; 3,987,193; 3,996,244; 4,100,298; 4,411,912 and 4,260,633.

The preferred α-cyano-3-phenoxybenzyl pyrethroids for use as pesticides are of the formula I where $R^1$ is hydrogen and W is 1-(2-chloro-4-trifluoromethylanilino)-2-methylpropyl, α-isopropyl-4-chlorobenzyl, 2,2,3,3-tetramethylcyclopropyl, 2-(2,2-dichlorovinyl)-3,3-dimethylcyclopropyl or 2-(2,2,-dibromovinyl)-3,3-dimethylcyclopropyl.

For carrying out the process of the present invention, from 0.8 to 1.5 moles, preferably about 1.0 to 1.3 moles, of benzaldehyde (II) are employed per mole of carboxylic acid W—COOH.

The alkali or alkali earth metal cyanides are preferably chosen from the alkali metal cyanides such as sodium cyanide and potassium cyanide. Because of its availability and low cost, sodium cyanide is especially preferred. The cyanide salt is generally employed in at least equimolar amount, more generally in excess molar amount, the molar ratio of the cyanide salt to the aldehyde lying in the range of 1:1 to 1.6:1, preferably about 1:1 to 1.3:1.

The primary solvent is chosen from the acid acceptors such as pyridine, substituted pyridines such as picolines, or tertiary amines. Particularly preferred results are achieved with the picolines.

Aprotic solvents may optionally be used in combination with the primary, acid acceptor, solvent. Such aprotic solvents can be chosen from, but are not limited to benzene, toluene, hexane, tetrahydrofuran, N,N-dimethylformamide, N-methylpyrrolidinone, xylenes, and chlorinated hydrocarbons. Among these, toluene and/or N-methylpyrrolidinone are preferred. Any of the aforementioned solvents may be used singly or in combination with each other.

An esterification catalyst such as 4-dimethylaminopyridine may optionally be employed in step (b) of the process.

The sulfonyl halides utilized in step (b) of the present invention are conveniently selected from the $C_{1-4}$alkanesulfonyl halides, such as methanesulfonyl chloride and ethanesulfonyl bromide, and the arylsulfonyl halides, such as benzenesulfonyl chloride and toluenesulfonyl chloride. Due to its low cost and ready availability, methanesulfonyl chloride is preferred. The sulfonyl halide is generally employed in an excess molar amount, the molar ratio of the sulfonyl halide to the carboxylic acid lying in the range 1:1 to 1.5:1, preferably about 1.1:1 to 1.2:1.

Step (a) of the process of the present invention is carried out by mixing together all ingredients but the sulfonyl halide, maintaining the temperature of the reactants between 0° and 80° C., preferably between about 50° and 60° C., and stirring the reactants until the reaction is complete. In this reaction the carboxylic acid salt and the cyanohydrin of the aldehyde are formed.

This is followed immediately by step (b) wherein the reaction mixture is then cooled to between 0° and 50° C., preferably to about 0° to 20° C., and the sulfonyl halide is slowly added while maintaining a stable reaction temperature until the reaction is complete.

The compounds of formula (I) may be recovered from the reaction mixture in which they are formed by working up by established procedures.

The α-cyanobenzyl esters prepared by the process according to the present invention can exist in a number of stereoisomeric forms, and therefore the present invention includes the production of any one or a mixture of such stereoisomers. The required stereoisomer or mixture of stereoisomers may be obtained by using as starting material the appropriate stereoisomeric carboxylic acid. This process produces a 1:1 mixture of stereoisomers at the α-cyano carbon.

The following examples are provided to illustrate the practice of the present invention. Temperature is given in degrees Celsius.

EXAMPLE 1

A mixture of sodium cyanide (134.75 g, 2.75 mol), "mixed" picolines (>97% 3and 4-methylpyridine, obtained from Reilly Tar & Chemical Co.) (418.50 g, 4.50 mol), 3-phenoxybenzaldehyde (519.75 g, 2.54 mol), (R)-2-(2-chloro-4-trifluoromethylanilino)-3-methylbutanoic acid (738.37 g, 2.50 mol) in N-methylpyrrolidinone and 3750 ml of toluene is stirred for 3 hours, maintaining the reaction at 55°. The reaction mixture is then cooled to 7° with an ice bath, and methanesulfonyl chloride (327.75 g, 2.87 mol) is added slowly over 1 hour, while maintaining an internal temperature of 15°. The mixture is stirred at 15° for an additional 6 hours to complete esterification. (The completion of esterification is judged by GLPC on the disappearance of cyanohydrin.)

To the reaction mixture is added a solution of potassium hydroxide (241.0 g, 4.3 mol) in 2500 ml of water. After the solids have dissolved, the phases are separated and the organic phase is against washed with aqueous potassium hydroxide, with aqueous hydrochloric acid (2X) and then with water. The solvent is stripped to give, as an amber colored oil, (R,S)-α-cyano-3-phenoxybenzyl (R)-2-(2-chloro-4-trifluoromethylanilino)-3-methylbutanoate, in 90.48% yield (based on the weight of the starting butanoic acid).

EXAMPLE 2

Following the procedure of Example 1, to a mixture of 3-(2,2-dichlorovinyl)-2,2-dimethylcyclopropane-1-carboxylic acid (50 mmol), 3-phenoxybenzaldehyde (9.90 g, 50 mmol), N-methylpyrrolidinone (10 g) and "mixed" picolines (8.5 g) in toluene is added sodium cyanide (2.57 g, 52.5 mmol), followed ca. 3 hours later by slow addition of methanesulfonyl chloride (6.87 g, 60 mmol). The reaction mixture is worked up and the solvent is removed to give α-cyano-3-phenoxybenzyl 3-(2,2-dichlorovinyl)-2,2-dimethylcyclopropanecarboxylate.

EXAMPLE 3

A mixture of 4-(dimethylamino)pyridine (0.50 g, 0.0041 mol), sodium cyanide (13.50 g, 0.275 mol), 3-phenoxybenzaldehyde (51.05 g, 0.250 mol), (R)-2-(2-chloro-4-trifluoromethylanilino)-3-methylbutanoic acid (71.58 g, 0.242 mol) in N-methylpyrrolidinone and "mixed" picolines (obtained from Reilly Tar & Chemical Co.) (42.5 g, 0.455 mol) is heated with stirring to 55° for 2.5 hours. The reaction mixture is then cooled to 20° and hexane (100 ml) is added. Methanesulfonyl chloride (33.49 g, 0.293 mol) is added slowly over 1.75 hours while maintaining an internal reaction temperature of 15°-20°. After 2 hours at 20°, additional methanesulfonyl chloride (0.50 g, 0.004 mol) is added and the mixture is stirred for 1 hour. Then water (2.50 g) is added, followed 1 hour later by addition of hexane/toluene (80/20; 330 ml) and water (200 ml). The phases are separated and the organic phase is washed with water, with 10% aqueous HCl solution, with water, with 5% aqueous KOH solution, and with three portions of water. The solvent is stripped off to give (R,S)-α-cyano-3-phenoxybenzyl (R)-2-(2-chloro-4-trifluoromethylanilino)-3-methylbutanoate as an amber colored oil. Yield is 92.1% (based on the weight of the starting butanoic acid).

EXAMPLE 4

Following the procedure of Example 3, (R,S)-α-cyano-4-fluoro-3-phenoxybenzyl (R)-2-phenoxybenzyl (R)-2-(2-chloro-4-trifluoromethylanilino)-3-methylbutanoate is prepared from (R)-2-(2-chloro-4-trifluoromethylanilino)-3-methylbutanoic acid, 4-fluoro-3-phenoxybenzaldehyde and sodium cyanide. Yield is 93.03%, based on starting butanoic acid.

EXAMPLES 5–12

Following the procedure of Example 3, (R,S)-α-cyano-3-phenoxybenzyl (R)-2-(2-chloro-4-trifluoromethylanilino)-3-methylbutanoate is prepared from 3-phenoxybenzaldehyde and (R)-2-(2-chloro-4-trifluoromethylanilino)-3-methylbutanoic acid and a cyanide source in the presence of the substituents listed under Table A.

TABLE A

ADDITIONAL EXAMPLES FOLLOWING THE PROCEDURE OF EXAMPLE 3

| Ex. | Cyanide | Acid Acceptor Solvent | Aprotic Solvent | Yield (%) |
|---|---|---|---|---|
| 5 | NaCN | pyridine | toluene | 86 |

TABLE A-continued
ADDITIONAL EXAMPLES FOLLOWING THE PROCEDURE OF EXAMPLE 3

| Ex. | Cyanide | Acid Acceptor Solvent | Aprotic Solvent | Yield (%) |
|---|---|---|---|---|
| 6 | NaCN | dimethylaniline | hexane | 71 |
| 7 | NaCN | 5-ethyl-2-methyl-pyridine | hexane | 85 |
| 8 | NaCN | pyridine | hexane/toluene (6:1) | 91 |
| 9 | NaCN | 2,4,6-collidine | toluene | 89 |
| 10 | NaCN | triethylamine | hexane/toluene | 64 |
| 11 | NaCN | "mixed" picolines | methylene chloride | 88 |
| 12 | KCN | "mixed" picolines | toluene | 86 |

What is claimed is:

1. A process for the preparation of an α-cyano ester of formula (A):

wherein W is selected from:
(i) an optionally substituted cycloalkyl group of formula III

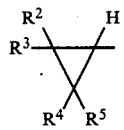

wherein,
each of $R^2$ and $R^3$ is independently $C_{1-6}$alkyl or halogen; or $R^2$ represents hydrogen, and $R^3$ represents $C_{1-6}$alkyl, $C_{1-6}$haloalkyl, $C_{2-6}$alkenyl or $C_{2-6}$haloalkenyl; and
each of $R^4$ and $R^5$ is independently $C_{1-6}$alkyl; or $R^4$ is hydrogen and $R^5$ is $C_{1-6}$alkyl, $C_{1-6}$haloalkyl, $C_{2-6}$alkenyl or $C_{2-6}$haloalkenyl;
(ii) an optionally substituted benzyl group of formula IV

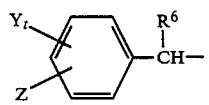

wherein,
$R^6$ is $C_{1-6}$alkyl or cyclopropyl;
t is zero, one or two; and
each of Y and Z is independently hydrogen, $C_{1-6}$alkyl, $C_{1-6}$haloalkyl, $C_{1-6}$alkoxy, $C_{1-6}$haloalkoxy, halogen, or nitro; or
(iii) an optionally substituted anilinoalkyl group of formula V

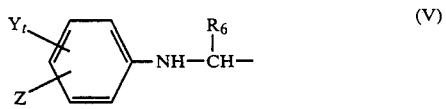

wherein, the values of $R^6$, t, Y and Z are as defined in (ii) above;
and Ar is

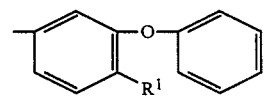

wherein, $R^1$ is hydrogen or fluoro;
which process comprises
(a) treating a carboxylic acid of formula W—COOH and an aldehyde of formula (II)

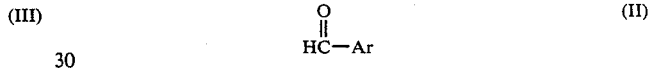

with an alkali or alkaline earth metal cyanide in an acid acceptor solvent and, optionally, an aprotic solvent, and
(b) treating the resulting mixture with a sulfonyl halide.

2. A process according to claim 1, wherein the acid acceptor solvent is selected from pyridine, picolines or tertiary amines.

3. A process according to claim 2 wherein the cyanide is an alkali earth metal cyanide.

4. A process according to claim 3 wherein the cyanide is sodium cyanide.

5. A process according to claim 4 wherein the acid acceptor solvent is picoline.

6. A process according to claim 5 wherein the sulfonyl halide is methanesulfonyl chloride.

7. A process according to claim 6 wherein the aldehyde is 3-phenoxybenzaldehyde.

8. A process according to claim 7 wherein the carboxylic acid is (R)-2-(2-chloro-4-trifluoromethylanilino)-3-methylbutanoic acid.

* * * * *